United States Patent
Swager et al.

(10) Patent No.: US 10,252,231 B2
(45) Date of Patent: Apr. 9, 2019

(54) COMPOSITIONS AND METHODS FOR FORMING EMULSIONS

(71) Applicant: Massachusetts Institute of Technology, Cambridge, MA (US)

(72) Inventors: Timothy M. Swager, Newton, MA (US); Edmundo Daniel Blankschtein, Brookline, MA (US); Lauren Dell Zarzar, Cambridge, MA (US); Vishnu Sresht, Cambridge, MA (US); Ellen Sletten, Somerville, MA (US); Julia Ann Kalow, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/929,117

(22) Filed: Oct. 30, 2015

(65) Prior Publication Data

US 2016/0151753 A1    Jun. 2, 2016

Related U.S. Application Data

(60) Provisional application No. 62/073,896, filed on Oct. 31, 2014.

(51) Int. Cl.
| | | |
|---|---|---|
| *B01F 17/00* | (2006.01) | |
| *B01F 17/14* | (2006.01) | |
| *B01F 17/54* | (2006.01) | |
| *C08L 35/02* | (2006.01) | |

(52) U.S. Cl.
CPC .......... *B01F 17/00* (2013.01); *B01F 17/0014* (2013.01); *B01F 17/0035* (2013.01); *B01F 17/0071* (2013.01); *C08L 35/02* (2013.01); *A23V 2002/00* (2013.01)

(58) Field of Classification Search
CPC . A23V 2002/00; B01F 17/00; B01F 17/0035; C08L 35/02
USPC .................. 424/401, 400; 426/654; 514/772; 522/79
See application file for complete search history.

(56) References Cited

U.S. PATENT DOCUMENTS

| | | |
|---|---|---|
| 4,870,026 A | 9/1989 | Wands et al. |
| 4,912,034 A | 3/1990 | Kalra et al. |
| 5,217,648 A | 6/1993 | Beissinger et al. |
| 5,332,661 A | 7/1994 | Adamczyk et al. |
| 5,516,635 A | 5/1996 | Ekins et al. |
| 5,980,936 A | 11/1999 | Krafft et al. |
| 6,180,418 B1 | 1/2001 | Lee |
| 6,710,092 B2 | 3/2004 | Scher et al. |
| 7,067,590 B2 | 6/2006 | Sato et al. |
| 7,625,951 B2 | 12/2009 | Daunert et al. |
| 7,767,017 B2 | 8/2010 | Lahann et al. |
| 7,947,772 B2 | 5/2011 | Lahann et al. |
| 8,241,651 B2 | 8/2012 | Lahann |
| 10,005,058 B2 | 6/2018 | Swager et al. |
| 2002/0040065 A1 | 4/2002 | Scher et al. |
| 2004/0069857 A1 | 4/2004 | Leblans et al. |
| 2004/0176479 A1 | 9/2004 | Scher et al. |
| 2006/0201390 A1 | 9/2006 | Lahann et al. |
| 2007/0237800 A1 | 10/2007 | Lahann |
| 2008/0242774 A1 | 10/2008 | Lahann et al. |
| 2009/0232856 A1 | 9/2009 | Patel |
| 2009/0306311 A1 | 12/2009 | Reed |
| 2010/0062525 A1 | 3/2010 | Abbott et al. |
| 2011/0104777 A1 | 5/2011 | Marquez et al. |
| 2012/0248020 A1 | 10/2012 | Granick et al. |
| 2012/0288852 A1 | 11/2012 | Willson et al. |
| 2012/0319043 A1 | 12/2012 | Stepien et al. |
| 2012/0328654 A1 | 12/2012 | Huang et al. |
| 2014/0016177 A1 | 1/2014 | Aizenberg et al. |
| 2014/0227684 A1 | 8/2014 | Hindson et al. |
| 2014/0350168 A1 | 11/2014 | Bormashenko |
| 2015/0238636 A1 | 8/2015 | Homyk et al. |
| 2016/0151756 A1 | 6/2016 | Swager et al. |
| 2018/0080927 A1 | 3/2018 | Swager et al. |

FOREIGN PATENT DOCUMENTS

| | | |
|---|---|---|
| WO | WO 1992/17179 A1 | 10/1992 |
| WO | WO 1995/31500 A2 | 11/1995 |
| WO | WO 2009/061372 A1 | 5/2009 |
| WO | WO 2009/101113 A2 | 8/2009 |
| WO | WO 2015/051179 A1 | 4/2015 |

OTHER PUBLICATIONS

Shah et al.; title: Janus supraparticles by induced phase separation of nanoparticles in droplets; Advanced Materials, 21, 1949-1953; published Feb. 27, 2009.*
International Search Report and Written Opinion for PCT/US2015/058268, dated Jan. 22, 2016.
International Search Report and Written Opinion for PCT/US2015/058286 dated Jan. 22, 2016.
Besnard et al., Multiple emulsions controlled by stimuli-responsive polymers. Adv Mater. May 28, 2013;25(20):2844-8. doi: 10.1002/adma.201204496. Epub Mar. 11, 2013.
McClements et al., Factors that affect the rate of oil exchange between oil-in-water emulsion droplets stabilized by a nonionic surfactant: Droplet size, surfactant concentration, and ionic strength. J. Phys. Chem. Jun. 1993; 97(28): 7304-08. doi: 10.1021/j100130a030.
Tanaka et al., Dual stimuli-responsive "mushroom-like" Janus polymer particles as particulate surfactants. Langmuir. Jul. 20, 2010;26(14):11732-6. doi: 10.1021/la101237c.

(Continued)

*Primary Examiner* — Yanzhi Zhang
(74) *Attorney, Agent, or Firm* — Wolf, Greenfield & Sacks, P.C.

(57) ABSTRACT

The present invention generally relates to compositions and methods for forming droplets and/or emulsions. In some embodiments, the compositions and methods comprise two or more components miscible at a first temperature and immiscible at a second temperature, dispersed in an outer phase.

14 Claims, 9 Drawing Sheets

(56) References Cited

OTHER PUBLICATIONS

Tu et al., One-step encapsulation and triggered release based on Janus particle-stabilized multiple emulsions. Chem Commun (Camb). Dec. 21, 2014;50(98):15549-52. doi: 10.1039/c4cc07854c. Epub Oct. 30, 2014.
Yusa et al., Fluorescence Studies of pH-Responsive Unimolecular Micelles Formed from Amphiphilic Polysulfonates Possessing Long-Chain Alkyl Carboxyl Pendants. Macromolecules. 2002; 35(27): 10182-88. doi: 10.1021/ma0212947. Epub Nov. 27, 2002.
U.S. Appl. No. 14/929,131, filed Oct. 30, 2015, Swager et al.
PCT/US2015/058268, Jan. 22, 2016, International Search Report and Written Opinion.
PCT/US2015/058286, Jan. 22, 2016, International Search Report and Written Opinion.
Augustin et al., Nano- and micro-structured assemblies for encapsulation of food ingredients. Chem Soc Rev. Apr. 2009;38(4):902-12. doi: 10.1039/b801739p. Epub Dec. 4, 2008.
Bedford et al., Solubilities and volume changes attending mixing for the system: perfluoro-n-hexane-n-hexane. J Am Chem Soc. 1958. 80: 282-5.
Brown et al., Stimuli-responsive surfactants. Soft Matter. 2013. 9: 2365-74.
Chakravarti et al., Liquid membrane multiple emulsion process of chromium (VI) separation from waste waters. Colloid Surface A 1995, 103:59-71.
Chen et al., Photoresponsive monodisperse cholesteric liquid crystalline microshells for tunable omnidirectional lasing enabled by a visible light-driven chiral molecular switch. Adv Opt Mater. 2014.
Chevallier et al., Photofoams: remote control of foam destabilization by exposure to light using an azobenzene surfactant. Langmuir. Feb. 7, 2012;28(5):2308-12. doi: 10.1021/la204200z. Epub Jan. 27, 2012.
Choi et al., Microfluidic design of complex emulsions. Chem Phys Chem. 2014. 15: 21-9.
Choi et al., One step formation of controllable complex emulsions: from functional particles to simultaneous encapsulation of hydrophilic and hydrophobic agents into desired position. Adv mater. 2013; 6 pages.
Dominguez et al., Modeling and understanding the vapour-liquid and liquid-liquid interfacial properties for the binary mixture of n-heptane and perfluoro-n-hexane. J Mol Liq. 2013. 185: 36-43.
Engel et al, Insulin: intestinal absorption as water-in-oil-in-water emulsions. Nature. Aug. 24, 1968;219(5156):856-7.
Gao et al., Double emulsion templated microcapsules with single hollow cavities and thickness-controllable shells. Langmuir. Apr. 9, 2009;25(6):3832-8. doi: 10.1021/la804173b.
Gladysz et al., Structural, physical and chemical properties of fluorous compounds. Top Curr Chem. 2012. 308: 1-24.
Gresham et al., Use of a sustained-release multiple emulsion to extend the period of radio protection conferred by cysteamine. Nature. Nov. 19, 1971;234(5325):149-50.
Guo et al., Double emulsion templated microcapsules with single hollow cavities and thickness-controllable shells. Langmuir. 2009;25:3832-3838.
Guzowski et al., The structure and stability of multiple microdroplets. Soft Matter. 2012. 8: 7269-78.
Haase et al., Tailoring of high-order multiple emulsions by the liquid-liquid phase separation of ternary mixtures. Angew Chem Int Ed. 2014;53:1-6.
Kim et al., Fabrication of monodisperse gel shells and functional microshells in microfluidic devices. Angew Chem Int Ed. 2007. 119: 1851-4.
Lemal et al., Perspective on fluorocarbon chemistry. J Org Chem. Jan. 9, 2004;69(1):1-11.
Lone et al., Fabrication of polymeric janus particles by droplet microfluidics. RSC Advances. 2014. 13322-13333.
McClain et al., Interfacial roughness in a near-critical binary fluid mixture: X-ray reflectivity and near-specular diffuse scattering. Eur Phys J B. 1999. 10: 45-52.
Mukerjee et al., Adsorption of fluorocarbon and hydrocarbon surfactants to air-water, hexane-water, and perfluorohexane-water interfaces. Relative affinities and fluorocarbon-hydrocarbon nonideality effects. J Phys Chem. 1981. 85: 2298-303.
Nie et al., Janus and ternary particles generated by microfluidic synthesis: design, synthesis, and self-assembly. J Am Chem Soc. Jul. 26, 2006;128(29):9408-12.
Patravale et al., Novel cosmetic delivery systems: an application update. Int J Cosmet Sci. Feb. 2008;30(1):19-33. doi: 10.1111/j.1468-2494.2008.00416.x.
Riess, Overview of progress in the fluorocarbon approach to in vivo oxygen delivery. Biomater Artif Cells Immobilization Biotechnol. 1992;20(2-4):183-202.
Schutt et al., Injectable microbubbles as contrast agents for diagnostic ultrasound imaging: the key role of perfluorochemicals. Angew Chem Int Ed Engl. Jul. 21, 2003;42(28):3218-35.
Shah et al., Designer emulsions using microfluidics. Mat Today. 2008. 11:18-27.
Shum et al., Droplet microfluidics for fabrication of non-spherical particles. Macromol Rapid Commun. Jan. 18, 2010;31(2):108-18. Doi: 10.1002/marc.200900590. Epub Nov. 24, 2009.
Song et al., Monodisperse w/w/w/ double emulsion induced by phase separation. Langmuir. 2012;28:12054-12059.
Utada et al., Monodisperse double emulsions generated from a microcapillary device. Science. Apr. 22, 2005;308(5721):537-41.
Wong et al., Bioinspired self-repairing slippery surfaces with pressure-stable omniphobicity. Nature. 2011. 477: 443-7.
Zhao et al., Microfluidic mass-transfer control for the simple formation of complex multiple emulsions. Angew Chem Int Ed. 2009;48:7208-11.
International Preliminary Report on Patentability dated May 11, 2017 for PCT/US2015/058268.
International Preliminary Report on Patentability dated May 11, 2017 for PCT/US2015/058286.
Berger et al., Stimuli-responsive bicomponent polymer Janus particles by "grafting from"/"grafting to" approaches. Macromolecules. 2008;41:9669-76. Epub Nov. 21, 2008.
Chen et al., Janus particles templated from double emulsion droplets generated using microfluidics. Langmuir. 2009;25(8):4320-3. Epub Mar. 18, 2009.
Choi et al., Patterned fluorescent particles as nanoprobes for the investigation of molecular interactions. Nano Letters. 2003;3(8):995-1000. Epub Jul. 11, 2003.
Kaufmann et al., "Sandwich" microcontact printing as a mild route towards monodisperse Janus particles with tailored bifunctionality. Adv Mater. 2011;23:79-83; Supporting Information pp. 1-8.
Kaufmann et al., Bifunctional Janus beads made by "sandwich" microcontact printing using click chemistry. J Mater Chem. 2012;22:6190-9. Epub Feb. 17, 2012.
Kumar et al., Multiple emulsions: A review. Int J Rec Adv Pharm Rsch. Jan. 2012; 2(1):9-19.
Li et al., Synthesis of biofunctional Janus particles. Macromol Rapid Comm. 2015;36:1200-4.
Nisisako et al., Synthesis of monodisperse bicolored Janus particles with electrical anisotropy using a microfluidic co-flow system. Adv Mater. 2006;18:1152-6.
Perro et al., Design and synthesis of Janus micro- and nanoparticles. J Mater Chem. 2005;15:3745-60. Epub Jul. 25, 2005.
Roh et al., Biphasic Janus particles with nanoscale anisotropy. Nat Mater. Oct. 2005;4:759-63. Epub Sep. 25, 2005.
Extended European Search Report dated Jun. 11, 2018 for Application No. EP 15855674.6.
International Search Report and Written Opinion dated Nov. 30, 2017 for Application No. PCT/US2017/052209.
Alino et al., Liquid crystal droplets as a hosting and sensing platform for developing immunoassays. Langmuir. Aug. 2011;27:11784-9.
Han et al., Retroreflective Janus microparticle as a nonspectroscopic optical immunosensing probe. ACS Appl Mater Interfaces. May 4, 2016;8(17):10767-74.

(56) References Cited

OTHER PUBLICATIONS

Niu et al., Optical biosensor based on liquid crystal droplets for detection of cholic acid. Optics Commun. 2016;381:286-91. Epub Jul. 22, 2016.
Wu et al., Bioinspired nanocorals with decoupled cellular targeting and sensing functionality. Small. 2010;6(4):503-7.
Zhang et al., Janus emulsions for the detection of bacteria. ACS Central Sci. Apr. 26, 2017;3(4):309-13.

* cited by examiner

COMPOSITIONS AND METHODS FOR FORMING EMULSIONS

RELATED APPLICATIONS

This application claims priority under 35 U.S.C. § 119(e) to U.S. Provisional Application Ser. No. 62/073,896, filed Oct. 31, 2014, which is incorporated herein by reference in its entirety for all purposes.

FIELD OF THE INVENTION

The present invention generally relates to emulsions and methods for forming emulsions.

BACKGROUND

Emulsification is a powerful age-old technique for mixing and dispersing immiscible components within a continuous liquid phase. Consequently, emulsions are central components of medicine, food, and performance materials. Complex emulsions, including multiple emulsions and Janus droplets, are of increasing importance in pharmaceuticals and medical diagnostics, in the fabrication of microdroplets and capsules for food, in chemical separations, for cosmetics, and for dynamic optics. As complex emulsion properties and functions are related to the droplet geometry and composition, the development of rapid and facile fabrication approaches allowing precise control over the droplets' physical and chemical characteristics is critical. Significant advances in the fabrication of complex emulsions have been accomplished by a number of procedures, ranging from large-scale less precise techniques that give compositional heterogeneity using high-shear mixers and membranes to small-volume microfluidic methods. However, improved materials and methods are needed.

SUMMARY OF THE INVENTION

The present invention provides emulsions and methods for forming emulsions.

In one aspect, emulsions are provided. In some embodiments, the emulsion comprises an outer phase, a plurality of droplets dispersed within the outer phase, wherein the plurality of droplets comprise two or more components, wherein the two or more components are substantially miscible at a first temperature, and wherein the two or more components are substantially immiscible at a second temperature.

In another aspect, methods for forming an emulsion are provided. In some embodiments, the method comprises adjusting the temperature of a fluid to a first temperature, wherein the fluid comprises a first phase and a second phase substantially immiscible in the first phase, wherein the second phase comprises two or more components that are substantially miscible with each other, emulsifying the fluid, and adjusting the temperature of the fluid to a second temperature, such that the two or more components become substantially immiscible.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control. If two or more documents incorporated by reference include conflicting and/or inconsistent disclosure with respect to each other, then the document having the later effective date shall control.

Figure 1A:
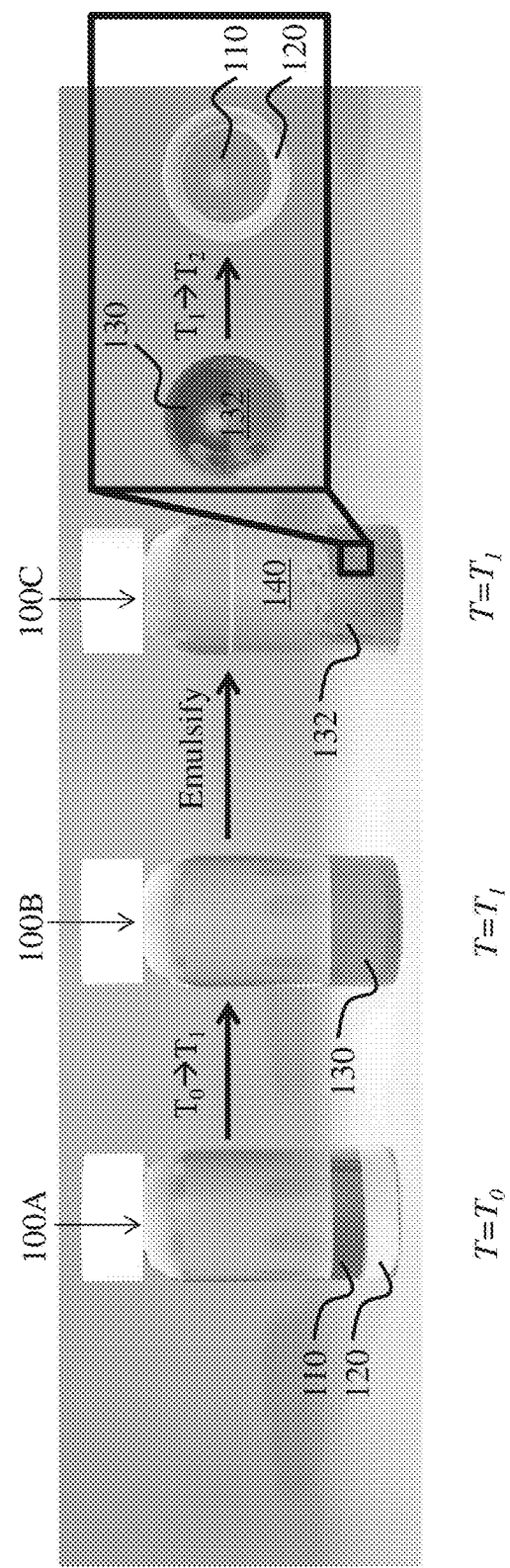
FIGS. 1A-1B illustrate the formation of complex emulsions, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein may be useful in the formation of emulsions (e.g., complex emulsions). The methods may allow for one-step fabrication of multi-phase (e.g., three-phase, four-phase) emulsions (e.g., complex emulsions), and may be useful in numerous applications including food manufacturing, drug delivery, medical diagnostics, performance materials, cosmetics, MRI and ultrasound contrast agents, artificial blood, among other applications. Furthermore, methods and emulsions described herein may allow for forming emulsions with controlled and reconfigurable morphologies. Another advantageous feature provided by emulsions and methods described herein is the ability to readily incorporate additional components (e.g., magnetic nanoparticles, biological materials, polymers, metals, etc.) into various applications. Emulsions (e.g., complex emulsions) are also provided.

In some embodiments, the methods and emulsions comprise an outer phase and a plurality of droplets dispersed within the outer phase. In certain embodiments, the plurality of droplets comprise two or more components. The two or more components may be substantially miscible over a range of temperatures (e.g., below a critical temperature, above a critical temperature). The two or more components may also be substantially immiscible over a different range of temperatures (e.g., above the critical temperature, below the critical temperature) than the range of temperatures over which they are miscible. The use of two or more components with differing miscibility at different temperatures may allow for the one-step formation (e.g., bulk) of emulsions (e.g., complex emulsions), unconstrained by the limits of previous methods (e.g., low yield of microfluidic devices, multi-step processes, the need for solvent addition and/or extraction, etc.)

In some embodiments, the plurality of droplets comprise two or more components, wherein the two or more components are immiscible below or above a critical temperature. In some embodiments, the critical temperature is an upper consolute temperature of the two or more components. That is to say, in some such embodiments, the two components are substantially miscible above the upper consolute temperature of the two or more components and substantially immiscible below the upper consolute temperature of the two or more components. In some embodiments, the critical temperature is a lower consolute temperature of the two or more components. That is to say, in some such embodiments, the two components are substantially miscible below the lower consolute temperature of the two or more components and substantially immiscible above the lower consolute temperature of the two or more components. In some embodiments, the miscibility of the two or more components is reversible. That is to say, the miscibility of the two or more components can be changed, in some embodiments, by increasing or decreasing the temperature to a temperature greater than, or less than, the critical temperature.

In some embodiments, two or more components may have an upper consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the upper consolute temperature of the two or more components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a upper consolute temperature of greater than or equal to about 0° C. and less than about 70° C.). Other ranges are also possible. Those skilled in the art would be capable of selecting suitable methods for determining the upper consolute temperature of two or more components.

In some embodiments, two or more components may have a lower consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the lower consolute temperature of two components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a lower consolute temperature of greater than or equal to about 0° C. and less than about 70° C.). Other ranges are also possible. Those skilled in the art would be capable of selecting suitable methods for determining the lower consolute temperature of two or more components.

In some embodiments, the two or more components have a greater miscibility at a first temperature as compared to a second temperature. That is to say, at the first temperature, the two or more components may be miscible to some extent, and miscible to some lesser extent (e.g., immiscible to some extent) at the second temperature.

In some cases, the two or more components may be substantially miscible over a range of pressures (e.g., below a critical pressure, above a critical pressure). The two or more components may also be substantially immiscible over a different range of pressure (e.g., above the critical pressure, below the critical pressure) than the range of pressures over which they are miscible. The use of two or more components with differing miscibility at different pressures may allow for the one-step formation (e.g., bulk) of emulsions (e.g., complex emulsions), unconstrained by the limits of previous methods (e.g., low yield of microfluidic devices, multi-step processes, the need for solvent addition and/or extraction, etc.)

Those skilled in the art would be capable of selecting a suitable temperature and/or suitable pressure range for forming the emulsions described herein based upon the teachings of the specification and the examples below, and would generally understand these temperature ranges and/or pressure ranges to include ranges in which the two or more components remain substantially fluid (e.g., below the boiling point of the two or more components, above the freezing point of the two or more components.) In some embodiments, the two or more components are immiscible with the outer phase over the suitable temperature range and/or pressure range.

Immiscible, as used herein, refers to two components (or a phase and a component) having an interfacial tension of greater than or equal to 0.01 mN/m as determined by an inverted pendant drop goniometer. Conversely, miscible, as used herein, refers to two components (or a phase and a component) having an interfacial tension of less than 0.01 mN/m as determined by an inverted pendant drop goniometer.

In some embodiments, at a temperature (and/or pressure) wherein the two or more components are immiscible, the two or more components comprise a first component and a second component at least partially encapsulated within the first component. In certain embodiments, at a temperature (and/or pressure) wherein the two or more components are immiscible, the two or more components do not encapsulate each other but interface with the outer phase (or an additional component at least partiallyencapsulating the two or more components) to form Janus droplets. Janus droplets are generally droplets where the droplet is divided into two or more distinct parts comprising two or more different components that do not encapsulate each other. For example, in some embodiments, the emulsion comprises an aqueous phase and a plurality of droplets comprising a hydrocarbon and a fluorocarbon, wherein the plurality of droplets are Janus droplets.

The term component, as used herein, generally refers to a portion of a droplet comprising a group of substantially similar molecules, a group of substantially similar compounds, and/or a phase (e.g., a non-aqueous phase, an aqueous phase). Those skilled in the art would understand that is not intended to refer to single molecules or atoms. In some embodiments, the component is a liquid phase (e.g., a gas phase, an aqueous phase, a non-aqueous phase) comprising a group of substantially similar compounds and/or molecules. For example, in some cases, each component may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more components.

In some embodiments, at least one of the two or more components comprises a hydrocarbon. Non-limiting examples of suitable hydrocarbons include alkanes (e.g., hexane, heptane, decane, dodecane, hexadecane), alkenes, alkynes, aromatics (e.g., benzene, toluene, xylene, benzyl benzoate, diethyl phalate), oils (e.g., natural oils and oil mixtures including vegetable oil, mineral oil, and olive oil), liquid monomers and/or polymers (e.g., hexanediol diacrylate, butanediol diacrylate, polyethylene glycols, trimethylolpropane ethoxylate triacrylate), alcohols (e.g., butanol, octanol, pentanol, ethanol, isopropanol), ethers (e.g., diethyl ether, diethylene glycol, dimethyl ether), dimethyl formamide, acetonitrile, nitromethane, halogenated liquids (e.g., chloroform, dichlorobenzene, methylene chloride, carbon tetrachloride), brominated liquids, iodinated liquids, lactates (e.g., ethyl lactate), acids (e.g., citric acid, acetic acid), liquid crystals (4-cyano-4'-pentylbiphenyl), trimethylamine, liquid crystal hydrocarbons (e.g., 5-cyanobiphenyl), combinations thereof, and derivatives thereof, optionally substituted. In some embodiments, the hydrocarbon comprises a halogen group, sulfur, nitrogen, phosphorous, oxygen, or the like. Other hydrocarbons are also possible.

In some embodiments, at least one of the two or more components comprises a fluorocarbon. Non-limiting examples of suitable fluorocarbons include fluorinated compounds such as perfluoroalkanes (e.g., perfluorohexanes, perfluorooctane, perfluorodecalin, perfluoromethylcyclohexane), perfluoroalkenes (e.g., perfluorobenzene), perfluoroalkynes, and branched fluorocarbons (e.g., perfluorotributylamine). Additional non-limiting examples of suitable fluorocarbons include partially fluorinated compounds such as methoxyperfluorobutane, ethyl nonafluorobutyl ether, 2H,3H-perfluoropentane, trifluorotoluene, perfluoroidodide, fluorinated or partially fluorinated oligomers, 2,2,3,3,4,4,5,5,6,6,7,7,8,8,9,9-hexadecafluorodecane-1,10-diyl bis(2-methylacrylate), perfluoroiodide, and 2-(trifluoromethyl)-3-thoxydodecafluorohexane. Other fluorocarbons are also possible.

In some embodiments, at least one of the two or more components comprises a silicone such as silicone oil. Non-limiting examples of suitable silicone oils include polydimethylsiloxane and cyclosiloxane fluids.

In some embodiments, at least one of the two or more components comprises water.

In some embodiments, at least one of the two or more components comprises an ionic liquid (e.g., an electrolyte, a liquid salt). In some embodiments, at least one of the two or more inner phases comprises an ionic liquid (e.g., an electrolyte, a liquid salt, 1-allyl-3-methylimidazolium bromide, 1-allyl-3-methylimidazolium chloride, 1-benzyl-3-methylimidazolium hexafluorophosphate, 1-butyl-1-methylpyrrolidinium hexafluorophosphate). In some embodiments, the outer phase comprises water. In certain embodiments, at least one of the two or more components comprises a deuterated compound (e.g., a deuterated hydrocarbon).

In some embodiments, at least one of the two or more components comprises a chlorinated solvent (e.g. chloroform, carbon tetrachloride).

In some embodiments, at least one of the two or more components comprises a polymer (e.g., polyethylene glycol). In certain embodiments, the polymer is a block copolymer. In certain embodiments, the polymer is a liquid crystal polymer (e.g., a thermotropic liquid crystal polymer). In certain embodiments, the polymer is a biopolymer (e.g. gelatin, alginate)

Non-limiting examples of combinations of components present in the emulsion described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a gas (e.g., a perfluoropentane gas).

In some embodiments, at least one of the two or more components comprises a combination of the materials described above (e.g., comprising a hydrocarbon, a fluorocarbon, a silicone, or combinations thereof). Non-limiting examples of combinations of components present in the emulsion described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a combination of the materials described above (e.g., comprising a hydrocarbon, a fluorocarbon, a silicone, or combinations thereof).

Those skilled in the art would be capable of selecting suitable components based upon the teachings of the specification and the examples below such that the two or more components are miscible under a given range of temperatures and are immiscible under a different range of temperatures, as described above.

The outer phase may comprise any suitable material. Generally, the two or more components comprising the plurality of droplets may be substantially immiscible with the outer phase. In some embodiments, the outer phase is an aqueous phase (e.g., comprising water). In certain embodiments, the outer phase is a non-aqueous phase. In some embodiments, the non-aqueous phase comprises a hydrocarbon, a fluorocarbon, a silicone, or the like, as described above in the context of the two or more components, substantially immiscible with the two or more components. Those skilled in the art would be capable, based upon the teachings of the specification and the examples below, of selecting suitable materials for use as an outer phase based upon the miscibility of those materials (e.g., such that the two or more components are substantially immiscible with the outer phase). The use of an non-aqueous outer phase may be advantageous in certain applications where the emulsion is used in low humidity environments. For example, a plurality of droplets comprising fluorocarbon/hydrocarbon phases can be created in a liquid silicone matrix. The silicone can be crosslinked of polymerized to change its mechanical properties. In some embodiments, at least a portion of the droplets may be deformed and/or aligned by mechanically deforming (e.g., applying a mechanical force to) the outer phase.

In some embodiments, the emulsion comprises an amphiphilic compound. In certain embodiments, the amphiphilic compound is miscible in the outer phase. In some embodiments, the amphiphilic compound is miscible in at least one of the two or more components. In certain embodiments, the amphiphilic compound has a greater miscibility in at least one of the two or more components than a miscibility in the outer phase. In some embodiments, the amphiphilic compound is disposed at the interface between the outer phase and the plurality of droplets. In certain embodiments, the amphiphilic compound is disposed at the interface between at least two of the two or more components. The amphiphilic compound may preferentially interact with one or more components or the outer phase. Those skilled in the art would be capable of selecting a suitable amphiphilic compound based upon the teachings of the specification and examples below.

In some embodiments, the amphiphilic compound is a surfactant. Non-limiting examples of suitable surfactants include ionic surfactants, non-ionic surfactants, and zwitterionic surfactants. In some embodiments, the surfactant is a fluorosurfactants (e.g., commercially available fluorosurfactants such as Zonyl® or Capstone®),. In certain embodiments, the surfactant is anionic surfactants (e.g., sodium dodecyl sulfate (SDS))., cationic surfactants (e.g., alkyltrimethyl ammonium chloride, alkylmethyl ammonium bromide), non-ionic surfactants (e.g., alkyl poly(ethylene oxide)), zwitterionic surfactants (e.g., alkyl betain, C8-lecitin), polymeric surfactants, gemini surfactants, particulate surfactants (e.g., graphene oxide, silica particles), and combinations thereof. Other surfactants are also possible. In some embodiments, the amphiphilic compound is a nucleic acid (e.g., DNA, RNA). In certain embodiments the amphiphilic compound comprises an amino acid (e.g., a peptide, a protein). In some embodiments, the amphiphilic compound comprises a biomaterial. Non-limiting examples of suitable biomaterials include carbohydrates or derivatives thereof, saccharides or derivatives thereof (e.g., sialic acid), lipids or derivatives thereof, enzymes, chromophores or the like. Those skilled in the art would be capable of selecting suitable biomaterials based upon the teachings of the specification and the examples below.

In some embodiments, the amphiphilic compound comprises a perfluorinated segment. In some embodiments, the amphiphilic compound comprises ethylene glycol.

In some embodiments, the amphiphilic compound is capable of forming metal complexes.

In certain embodiments, the amphiphilic compound is graphene oxide.

In some embodiments, the amphiphilic compound may be a particle (e.g., a silica particle, a polymer particle, a Janus particle, a nanoparticle, a gel particle).

In some embodiments, the one or more components and/or the outer phase comprises an additional compound dispersed in the one or more components and/or the outer phase. In certain embodiments, the additional compound is miscible dispersible in the a first component and immiscible not dispersible in the a second component. In some cases, at least a portion of the additional compound is dispersible in the first component and not dispersible in the second component (e.g., a surfactant). In some embodiments, the additional compound may be dispersible or not dispersible in the outer phase. Non-limiting examples of suitable additional compounds include particles (e.g., magnetic particles/nanoparticles, silica particles), biological molecules (e.g., insulin), pharmaceutical compounds, polymers, surfactants, cells, bacteria, viruses, active pharmaceutical ingredients, and metals or metal particles. Other additional compounds are also possible and those skilled in the art would be capable of selecting such compounds based upon the teachings of this specification.

In some embodiments, the emulsion can be formed by adjusting the temperature of a fluid comprising the outer phase and the two or more immiscible components such that the two or more components become substantially miscible with each other, and emulsifying the fluid (e.g., thus forming the plurality of droplets). In certain embodiments, the method comprises adjusting the temperature of the fluid comprising the plurality of droplets such that the two or more components become substantially immiscible.

For example, as illustrated in FIG. 1A, a fluid 100A comprises first component 110 (e.g., a hydrocarbon) and second component 120 (e.g., a fluorocarbon) which are immiscible at a first temperature $T_0$. In some embodiments, $T_0$ is adjusted to a second temperature $T_1$ (e.g., where $T_1$ is greater than $T_0$, or where $T_1$ is less than $T_0$) such that the first component and second component form a miscible mixture 130 in fluid 100B. For example, in some embodiments, the first component and the second component, which are initially substantially immiscible, may be heated such that they are miscible. In certain embodiments, the first component and the second component, which are initially substantially immiscible, may be cooled such that they are miscible. Miscible mixture 130 can, in certain embodiments, be emulsified to form emulsion 100C comprising plurality of droplets 132. Plurality of droplets 132 may comprise miscible mixture 130 and be present in an outer phase 140. In some cases, outer phase 140 may be added prior to changing the temperature from $T_0$ to $T_1$. In certain embodiments, outer phase 140 may be added after changing the temperature but prior to emulsification.

Figure 1B:
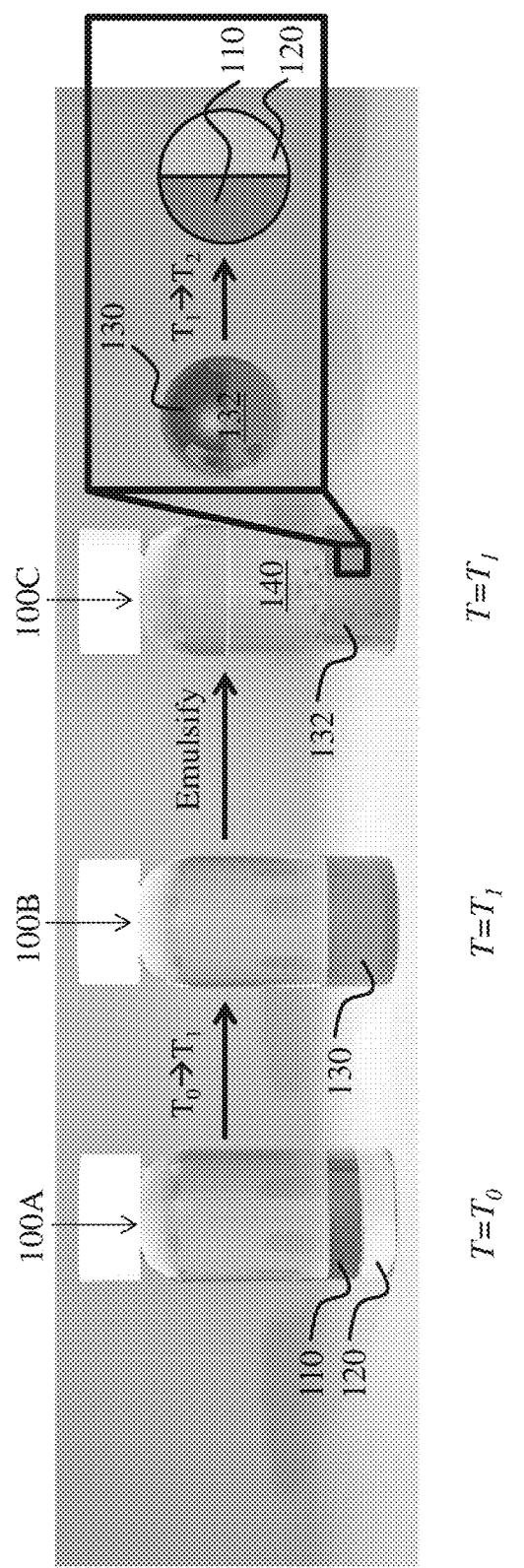

In some embodiments, $T_1$ is adjusted to a temperature $T_2$ (e.g., where $T_2$ is greater than $T_1$ or where $T_2$ is less than $T_1$) such that droplet 132 comprises first component 110, and second component 120 substantially immiscible with first component 110, contained within the droplet. In some such embodiments, first component 110 may be at least partially encapsulated by second component 120. In some embodiments, first component 110 and second component 120 are not encapsulated but form a Janus particle (FIG. 1B).

In some embodiments, $T_1$ is greater than a critical temperature of the two or more components (e.g., an upper consolute temperature of the two or more components). In certain embodiments, $T_1$ is less than a critical temperature of the two or more components (e.g., a lower consolute temperature). Those skilled in the art will be capable of selecting suitable methods for determining the critical temperature (e.g., the upper consolute temperature, the lower consolute temperature) of two or more components.

Suitable methods for emulsifying the fluid are known in the art and may comprise sonication, high shear mixing, shaking, passing the fluid through a membrane, or injecting the two or more components into the outer phase through a small diameter channel.

In some embodiments, a portion of the plurality of droplets can be solidified (e.g., polymerized) such that a first configuration, a second configuration different than the first configuration, and/or a Janus droplet configuration solid droplets can be fabricated. Those skilled in the art will be capable of selecting appropriate materials for solidifying droplets and may include, in some embodiments, adding a crosslinker (e.g., a fluorinated acrylate) to the colloid such that the crosslinker crosslinks at least one of the two or more component, wherein the at least one of the two or more component comprises a crosslinkable polymer . In certain embodiments, solidifying droplets comprises adding a gelling agent (e.g., calcium-crosslinked alginate, gelatin, agar, or the like). In some embodiments, solidifying droplets comprises drying the droplets. In certain embodiments, solidifying droplets comprises changing the temperature such that one or more components solidify (e.g., a component comprising a liquid crystal or liquid crystal polymer that solidifies below the new temperature, a component comprising a liquid with a relatively high freezing point such that changing the temperature solidifies the liquid). Other methods of solidifying droplets are also possible and are known in the art.

EXAMPLES

The following examples illustrate embodiments of certain aspects of the invention. It should be understood that the methods and/or materials described herein may be modified and/or scaled, as known to those of ordinary skill in the art.

Example 1

The following example describes the general formation of an emulsion. For example, hydrocarbon and fluorocarbon liquids were heated until miscible and emulsified. The temperature required varied depending on the solutions. Solutions were emulsified either in bulk by shaking or by coaxial glass capillary microfluidics and cooled to induce phase separation. For hexane-perfluorohexane emulsions, the emulsions were chilled on ice prior to imaging and often imaged while immersed in a cool water bath to maintain a temperature below 20° C. For microfluidics, syringe pumps were used to inject the outer phase and inner phase using a glass capillary microfluidic device made from an outer square capillary and inner cylindrical capillary pulled to a 30 µm tip using a Micropipette Puller (Sutter Instrument Company). The microfluidic setup was heated above the $T_c$ of the inner phase solution using a heat lamp. Emulsions were then cooled below $T_c$ to induce phase separation. Emulsions were observed to be stable during the time periods used (e.g., on the order days).

Example 2

The following example describes the formation of an emulsion. According to the methods described in Example 1.

Figure 2:
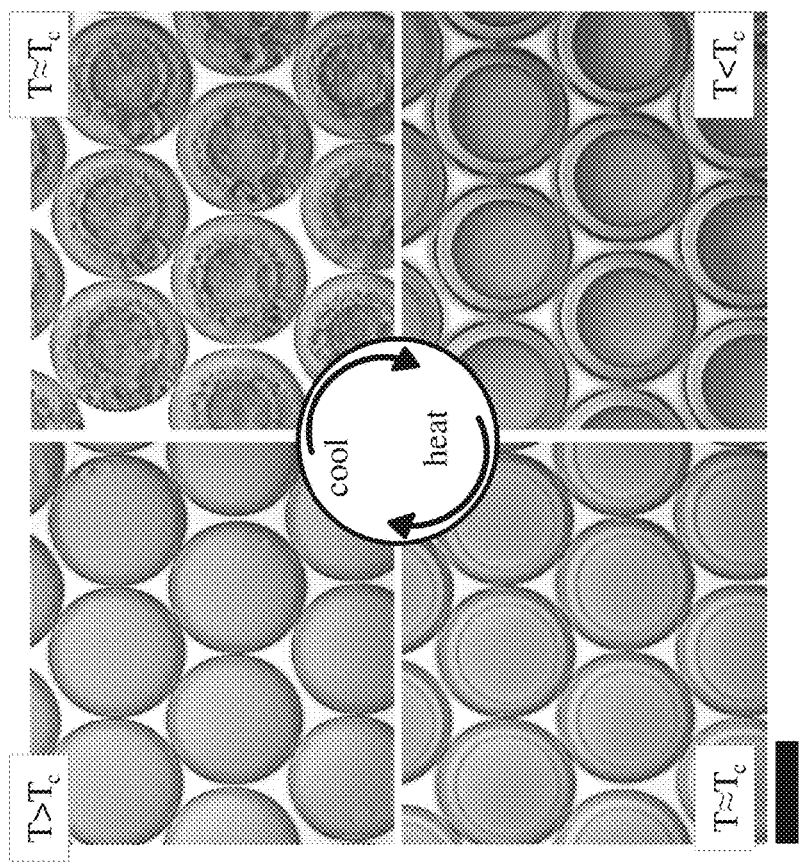
FIG. 2 shows photographs of the formation of complex emulsions comprising hexane and perfluorohexane, according to certain embodiments.
Figure 3A:
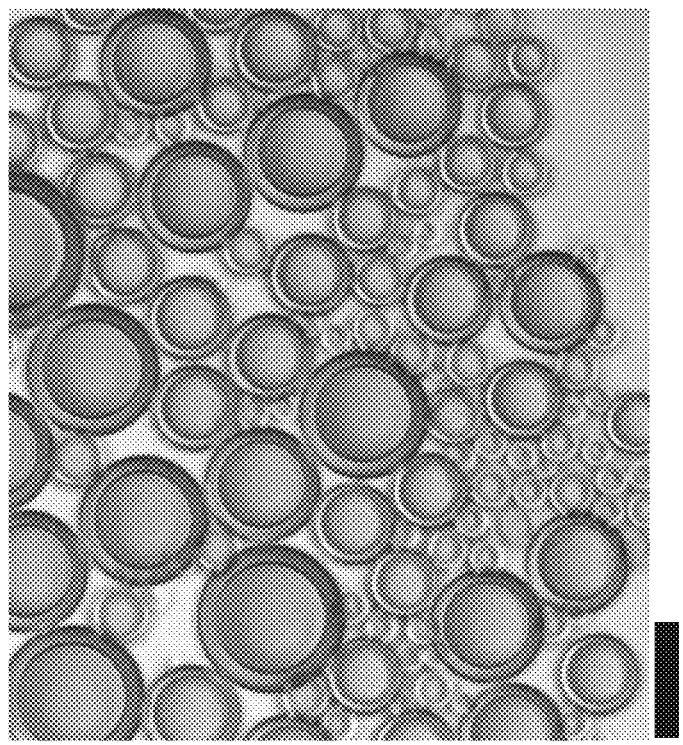
FIG. 3A shows photographs of a complex emulsion comprising hexane and perfluorohexane, formed according to one set of embodiments.
Figure 3B:
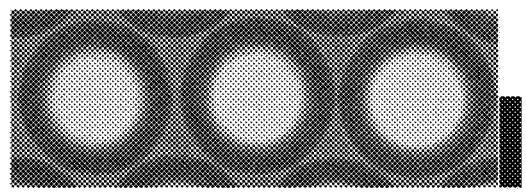
FIG. 3B shows a photograph of a complex emulsion comprising hexane and perfluorohexane, formed according to one set of embodiments.

Fluorocarbons are generally lipophobic as well as hydrophobic and many fluorocarbon and hydrocarbon liquids are immiscible at room temperature but have a low upper consolute temperature ($T_c$) and mix with gentle heating. Hexane and perfluorohexane, for example, have a $T_c$ of 22.65° C. A 1:1 volume ratio of hexane and perfluorohexane was mixed and emulsified above $T_c$ in an aqueous solution of Zonyl FS-300 fluorosurfactant (FIG. 2, top left). Cooling below $T_c$ induced phase separation and yielded structured complex droplets (FIGS. 2. Bottom right). Above $T_c$, hexane and perfluorohexane are miscible and emulsified in 0.1% Zonyl (FIG. 2, top left). Below $T_c$, hexane and perfluorohexane phase separate to create a hexane-in-perfluorohexane-in-water (H/F/W) double emulsion (FIG. 2, bottom right). This phase separation was reversible. These complex emulsions were readily produced in bulk by shaking warm hexane-perfluorohexane liquid in a surfactant solution (FIG. 3A). Although these droplets were polydisperse, the morphology and composition of the droplets was highly uniform. Chemical partitioning during phase separation gave directed compartmentalization of solutes (FIG. 3B), forming hexane/perfluorohexane/water double emulsion droplets in a microfluidic device. Therefore, temperature-induced phase separation of liquids provides a facile, scalable approach to fabrication of complex functional emulsions.

Example 3

The following example describes the formation of an emulsion comprising Janus droplets.

Figure 4A:
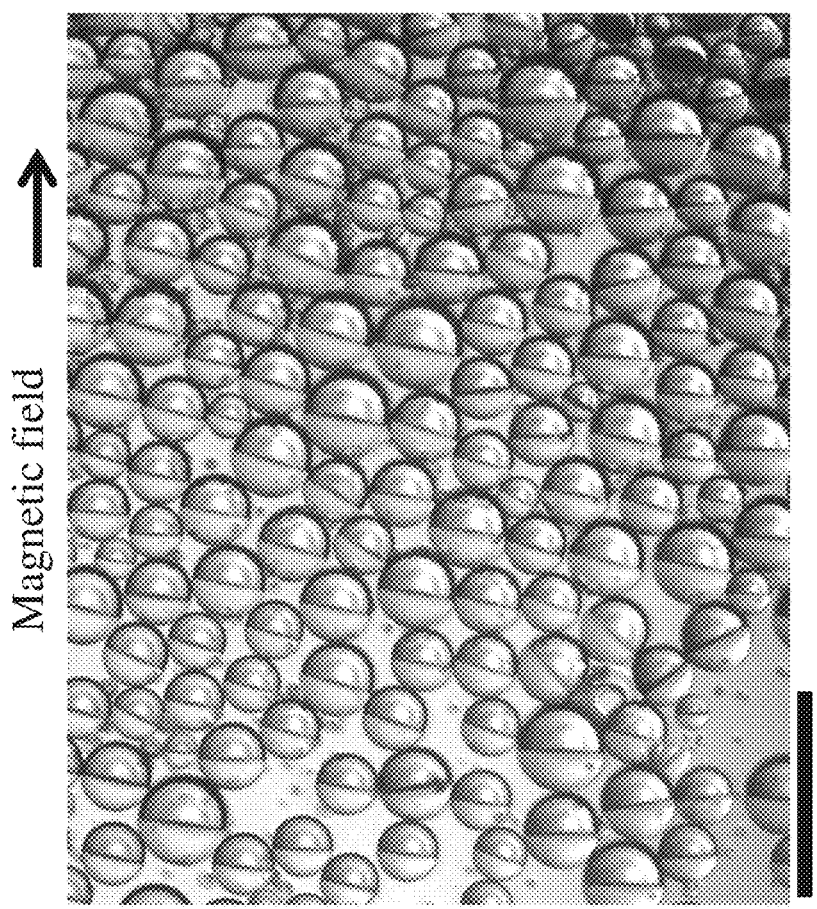
FIG. 4A shows a photograph of Janus droplets, formed according to one set of embodiments.

Liquid droplets and solid droplets with asymmetric properties were created by affecting different chemistries in the separate compartments of a fluorous-hydrocarbon Janus droplet. To create directionally-orientable and movable liquid Janus droplets, magnetic $Fe_3O_4$ nanoparticles stabilized with oleic acid were synthesized for preferential partitioning into the hydrocarbon phase. Magnetite nanoparticles were made as follows: 25 mL of concentrated NH3OH was added to an acidified solution of 1.6 g of $FeCl_3$ and 1 g of $FeCl_2 \cdot 4H_2O$ in 50 mL of water at 80° C. The magnetite nanoparticle precipitate was collected with a magnet, washed with water, and redispersed. 1 g of sodium oleate in 10 mL of water was added under stirring at room temperature. The oily black precipitate was extracted with hexanes. Solid was collected by evaporation of solvent and subsequently redispersed in dichlorobenzene. Janus droplets were obtained by heating the nanoparticle/dichlorobenzene solution and ethyl nonafluorobutyl ether above the Tc and shaking in 0.2% SDS and 0.2% Zonyl in a 2.5:1 ratio. The droplets were oriented using a neodymium magnet. Upon inclusion in a Janus emulsion of dichlorobenzene and ethyl nonafluorobutyl ether, the nanoparticle/dichlorobenzene hemispheres are rapidly oriented and move in the direction of a magnet (FIG. 4A).

Figure 4B:
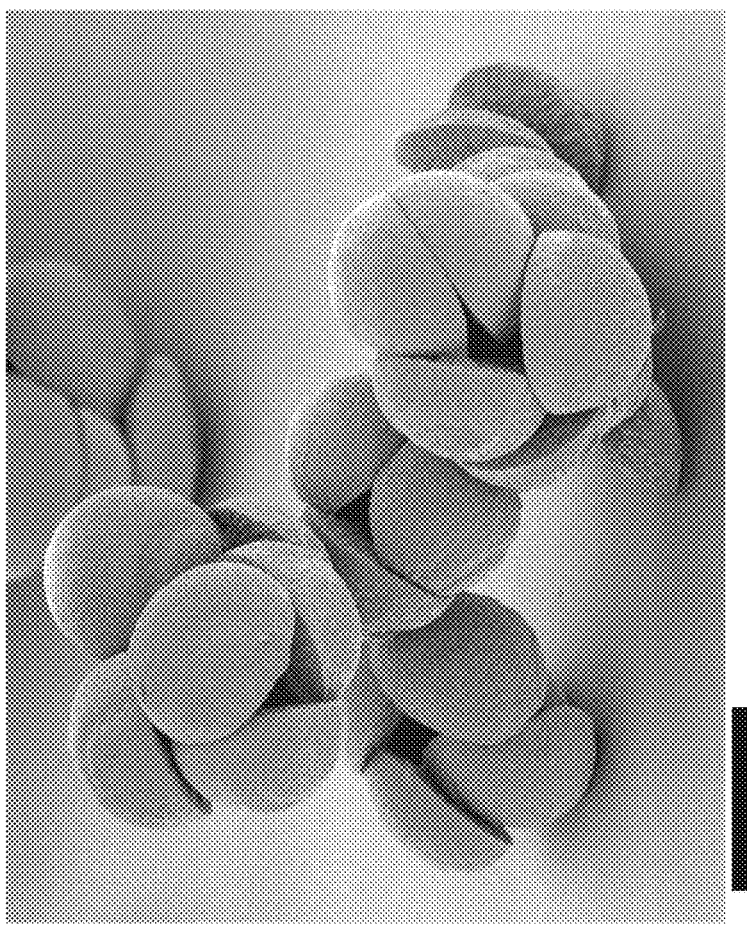
FIG. 4B shows a scanning electron micrograph of particles formed from polymerized Janus droplets, formed according to one set of embodiments.
Figure 4C:
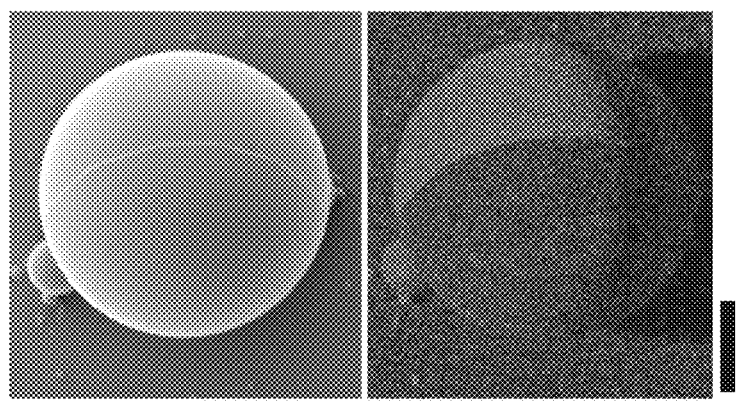
FIG. 4C shows a scanning electron micrograph (top) and an energy dispersive x-ray map highlighting fluorine (bottom) of a Janus particle, formed according to one set of embodiments.

To generate solid hemispherical droplets, an emulsion consisting of a liquid polymer precursor, 1,6-hexanediol diacrylate, as the hydrocarbon phase and methoxyperfluorobutane as the fluorous phase, was polymerized (FIG. 4B). 1-6 , hexanediol diacrylate with 4% Darocur 1173 photoinitiator was heated with equal volume methoxyperfluorobutane above the Tc and emulsified. 1% SDS and 1% Zonyl in a 3:2 ratio yielded Janus droplets which were then polymerized under a UV lamp while kept cold on ice. By replacing methoxyperfluorobutane with a fluorinated acrylate oligomer and crosslinker, spherical solid Janus droplets with fluorinated and non-fluorinated sides were created (FIG. 4C).

Example 4

Figure 5:
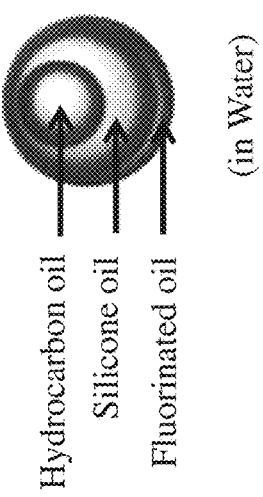
FIG. 5 shows a four-phase emulsion, formed according to one set of embodiments.

The same principles of droplet transformations observed in three-phase emulsions, and described in Example 1, were extended to a four-phase system thereby generating reconfigurable droplets of even higher order complexity. A system comprising of silicone oil (Si), hydrocarbon oil (H, mineral oil and octadecane), and fluorinated oil (F, ethyl nonafluorobutyl ether) was designed such that the liquids mixed with heating and separated into three phases at room temperature (FIG. 5). Light mineral oil with 20 wt % octadecane (used to reduce the Tc in a mixture with the other liquids), silicone oil, and ethyl nonafluorobutyl ether were used as the inner phases in a volume ratio of 6:7:13. The mineral oil and ethyl nonafluorobutyl ether both partitioned into the silicone oil such that upon phase separation, the silicone oil phase is enriched with some quantity of the two other phases. Aqueous mixtures of varying ratios of 1% Zonyl and 1% SDS were used as the outer phase, and emulsions were formed in the bulk by shaking.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method of forming an emulsion, comprising:
   adjusting the temperature of a fluid to a first temperature, wherein the fluid at the first temperature comprises an outer phase and a second phase immiscible in the outer phase, wherein the second phase comprises a first component and a second component that are miscible with each other;
   after adjusting the temperature of the fluid to the first temperature, emulsifying the fluid thereby forming a droplet comprising the first component and the second component, the droplet dispersed within the outer phase; and
   after emulsifying the fluid, adjusting the temperature of the fluid to a second temperature, such that the first component and the second component within the droplet become immiscible.

2. The method of claim 1, wherein the first temperature is greater than an upper consolute temperature of the two or more components.

3. The method of claim 1, wherein the second temperature is less than an upper consolute temperature of the two or more components.

4. The method of claim 1, wherein the first temperature is less than the second temperature.

5. The method of claim 4, wherein the first temperature is less than a lower consolute temperature of the two or more components.

6. The method of claim 4, wherein the second temperature is greater than a lower consolute temperature of the two or more components.

7. The method of claim 1, wherein at least one of the two or more components comprises a hydrocarbon, a fluorocarbon, a silicone, a thermotropic liquid crystal, water, an ionic liquid, or combinations thereof.

8. The method of claim 1, wherein each of the two or more components is a liquid.

9. The method of claim 1, wherein the temperature of the fluid to the second temperature is adjusted such that the two or more components comprise a first component and a second component at least partially encapsulated within the first component.

10. The method of claim 1, wherein emulsifying the fluid comprises emulsifying the fluid after adjusting the temperature of a fluid to the first temperature.

11. The method of claim 1, wherein the outer phase is an aqueous phase.

12. The method of claim 11, wherein the outer phase comprises a surfactant.

13. The method of claim 1, wherein the outer phase is a non-aqueous phase.

14. The method of claim 1, wherein after adjusting the temperature of the fluid to the second temperature, the droplet is a Janus droplet.

\* \* \* \* \*